(12) United States Patent
Wang et al.

(10) Patent No.: US 9,744,023 B2
(45) Date of Patent: Aug. 29, 2017

(54) EMBOLIC DEBRIS DEFLECTOR

(71) Applicant: BOSTON SCIENTIFIC SCIMED, INC., Maple Grove, MN (US)

(72) Inventors: Huisun Wang, Maple Grove, MN (US); James M. Anderson, Fridley, MN (US); Paul J. Miller, Vadnais Heights, MN (US); Justin Plessel, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1004 days.

(21) Appl. No.: 13/659,027

(22) Filed: Oct. 24, 2012

(65) Prior Publication Data
US 2013/0103075 A1 Apr. 25, 2013

Related U.S. Application Data

(60) Provisional application No. 61/551,062, filed on Oct. 25, 2011.

(51) Int. Cl.
*A61M 29/00* (2006.01)
*A61F 2/01* (2006.01)
(Continued)

(52) U.S. Cl.
CPC ............ *A61F 2/01* (2013.01); *A61B 17/22* (2013.01); *A61F 2/013* (2013.01); *A61B 2017/320012* (2013.01); *A61F 2002/011* (2013.01); *A61F 2230/0019* (2013.01); *A61F 2230/0023* (2013.01); *A61F 2230/0026* (2013.01)

(58) Field of Classification Search
CPC .... A61F 2/01; A61F 2/02; A61F 2/013; A61F 2/82; A61F 2/848; A61F 2002/011; A61F 2002/8483; A61F 2002/8486; A61F 2/06; A61F 2002/015; A61F 2002/016; A61F 2002/018; A61F 2002/061; A61F 2002/062; A61F 2002/068; A61B 17/12177;
(Continued)

(56) References Cited

U.S. PATENT DOCUMENTS 4,249,946 A 2/1981 Danielson
6,258,120 B1 7/2001 McKenzie et al.
(Continued)

FOREIGN PATENT DOCUMENTS

SE WO 2010026240 A1 * 3/2010 ............... A61F 2/01
WO 2007129323 A2 11/2007
WO 2010026240 A1 3/2010

*Primary Examiner* — Jonathan Miles
*Assistant Examiner* — Kankindi Rwego
(74) *Attorney, Agent, or Firm* — Seager, Tufte & Wickhem LLP (57) ABSTRACT

The disclosure pertains to debris diverters for use within the aorta and methods of diverting or redirecting emboli and other debris away from the carotid arteries to prevent cerebral embolization. The disclosure includes aortic diverters positionable in the ascending aorta in order to divert embolic material of all sizes away from the carotid arteries, thereby washing emboli downstream into the thoracic and peripheral vasculature. The debris diverters of the disclosure are adapted to be placed in the ascending and transverse aorta via the left subclavian artery in order to divert embolic material away from the carotid arteries and methods of use therefor.

12 Claims, 10 Drawing Sheets

(51) Int. Cl.
*A61B 17/22* (2006.01)
*A61B 17/32* (2006.01)

(58) Field of Classification Search
CPC .............. A61B 17/22; A61B 17/32; A61B 2017/320004; A61B 2017/320008; A61B 2017/320012
See application file for complete search history.

(56) References Cited

U.S. PATENT DOCUMENTS

| | | | |
|---|---|---|---|
| 6,361,545 B1 | 3/2002 | Macoviak et al. | |
| 6,371,935 B1 | 4/2002 | Macoviak et al. | |
| 6,395,014 B1 | 5/2002 | Macoviak et al. | |
| 6,669,680 B1 | 12/2003 | Macoviak et al. | |
| 6,695,864 B2 | 2/2004 | Macoviak et al. | |
| 6,997,939 B2 | 2/2006 | Linder et al. | |
| 7,083,633 B2 | 8/2006 | Morrill et al. | |
| 7,137,991 B2 | 11/2006 | Fedie | |
| 7,585,309 B2 | 9/2009 | Larson | |
| 7,604,650 B2 | 10/2009 | Bergheim | |
| 7,875,051 B2 | 1/2011 | Beulke et al. | |
| 8,114,114 B2 | 2/2012 | Belson | |
| 8,206,412 B2 | 6/2012 | Galdonik et al. | |
| 8,252,016 B2 | 8/2012 | Anwar | |
| 8,287,564 B2 | 10/2012 | Beulke et al. | |
| 8,308,754 B2 | 11/2012 | Belson | |
| 2003/0158571 A1 | 8/2003 | Esch et al. | |
| 2003/0158574 A1 | 8/2003 | Esch et al. | |
| 2005/0267516 A1* | 12/2005 | Soleimani | A61F 2/01 606/200 |
| 2006/0015138 A1 | 1/2006 | Gertner | |
| 2006/0052797 A1* | 3/2006 | Kanamaru | A61B 17/22 606/113 |
| 2006/0253148 A1 | 11/2006 | Leone et al. | |
| 2007/0027534 A1 | 2/2007 | Bergheim et al. | |
| 2008/0065145 A1 | 3/2008 | Carpenter | |
| 2009/0082800 A1 | 3/2009 | Janardhan | |
| 2009/0254172 A1* | 10/2009 | Grewe | A61F 2/856 623/1.15 |
| 2010/0076482 A1 | 3/2010 | Shu et al. | |
| 2010/0168785 A1 | 7/2010 | Parker | |
| 2010/0179583 A1 | 7/2010 | Carpenter et al. | |
| 2010/0179584 A1 | 7/2010 | Carpenter et al. | |
| 2010/0179585 A1 | 7/2010 | Carpenter et al. | |
| 2010/0179647 A1 | 7/2010 | Carpenter et al. | |
| 2010/0185231 A1 | 7/2010 | Lashinski | |
| 2010/0191276 A1 | 7/2010 | Lashinski | |
| 2010/0211095 A1 | 8/2010 | Carpenter | |
| 2010/0312268 A1 | 12/2010 | Belson | |
| 2010/0324589 A1 | 12/2010 | Carpenter et al. | |
| 2011/0022076 A1 | 1/2011 | Lashinski | |
| 2011/0282379 A1 | 11/2011 | Lee et al. | |
| 2011/0295304 A1 | 12/2011 | Jonsson | |
| 2012/0109182 A1 | 5/2012 | Belson | |
| 2012/0172915 A1 | 7/2012 | Fifer et al. | |
| 2012/0172916 A1 | 7/2012 | Fifer et al. | |
| 2012/0172917 A1 | 7/2012 | Fifer et al. | |
| 2012/0172918 A1 | 7/2012 | Fifer et al. | |
| 2012/0172919 A1 | 7/2012 | Fifer et al. | |
| 2012/0172920 A1 | 7/2012 | Fifer et al. | |
| 2012/0179033 A1 | 7/2012 | Merhi | |
| 2012/0289996 A1 | 11/2012 | Lee et al. | |

* cited by examiner

EMBOLIC DEBRIS DEFLECTOR

RELATED APPLICATIONS

This application claims the benefit of U.S. Provisional Application Ser. No. 61/551,062, filed Oct. 25, 2011.

BACKGROUND

Preventing emboli and other debris from entering the carotid arteries (i.e., the brachiocephalic artery, or right common carotid artery, and the left common carotid, and the left subclavian) by way of the aorta reduces the incidence of ischemic stroke. Emboli and other debris in the aorta come from several sources. These sources include: 1) aortic atheroma which detaches from the wall of the aorta due to various reasons including incising, clamping, and/or clamp release of the aorta during surgery; 2) debris released during surgery on the heart such as the installation of a replacement heart valve; 3) thrombus which forms in the right atrium resulting from atrial fibrillation; 4) thrombus which forms on ventricular assist devices; 5) venous thrombus which passes into the left ventricle through a patent foramen ovale or other arteriovenous shunt; and 6) other less common sources.

A variety of intravascular filtering means are known in the art and may consist of a flexible metallic grid, a flexible synthetic or plastic grid, a weave of synthetic filaments, or a nondegradable or possibly biodegradable textile cloth, often supported by a basket or funnel shaped frame which may be deployed within the lumen of a vessel to be protected.

There are fewer intravascular devices designed for arterial and especially aortic filtration, much less diversion. A filter that functions in arteries must address additional concerns because of the hemodynamic differences between arteries and veins. Arteries are much more flexible and elastic than veins and, in the arteries, blood flow is pulsatile with large pressure variations between systolic and diastolic flow. These pressure variations cause the artery walls to expand and contract. Thus, filters and diverters must be able to expand and contract along with the lumen of the aorta to which they may be anchored. In addition, intravascular devices for aortic filtration and/or diversion of emboli typically occlude a significant portion of the lumen of the aorta rendering them unsatisfactory for use in combination with other intravascular interventional procedures.

The problem of preventing emboli from reaching the cerebral vasculature has thus far not been adequately addressed. Therefore, a need exists for new devices and methods to prevent embolic material from entering the carotid/cerebral arteries, while maintaining peripheral blood flow from the heart to the descending aorta.

SUMMARY

This disclosure relates to debris diverters for use within the aorta and methods of diverting or redirecting emboli and other debris away from the carotid arteries to prevent cerebral embolization. The disclosure includes debris diverters positionable in the ascending aorta to divert embolic material of all sizes away from the carotid arteries, thereby washing emboli downstream into the thoracic and peripheral vasculature. The devices of the disclosure are adapted to be placed in the ascending and transverse aorta in order to divert embolic material and other debris away from the carotid arteries. This debris includes but is not limited to atheromatous fragments or material, thrombus, globules of fat, air bubbles, clumps of bacteria and/or other foreign matter, tumor cells, or any other bits of tissue.

The disclosure relates to a debris deflector comprising a support member and a porous deflection structure adapted to lie substantially along a longitudinal segment of an aortic arch while extending transversely about less than the entire circumference of the aorta, wherein the porous deflection structure comprises a single panel blood permeable membrane and a support structure.

In another embodiment, the disclosure relates to a system for preventing debris within the aorta from entering the right carotid artery and the left carotid artery, the system comprising a debris deflector and at least one of a delivery device for the debris deflector and a retrieval device for the debris deflector.

In yet another embodiment, the disclosure relates to a method of preventing debris within the aorta from entering the right carotid artery and the left carotid artery, the method comprising advancing a debris deflector through the left subclavian artery and into the aorta; deploying the debris deflector within the aorta generally upstream from left subclavian artery to cover the ostium of the brachiocephalic artery and or the ostium of the right common carotid artery, the ostium of the left common carotid artery, and at least a portion of the ostium of the left subclavian artery; performing at least one of a diagnostic procedure and a therapeutic procedure upstream of the aorta; retrieving the debris deflector; and removing the debris deflector from the left subclavian artery.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary.

Although portions of this disclosure may refer to covering one or the other of the ostium of brachiocephalic artery and the ostium of the right common carotid artery, it will be understood that those individual terms as used herein are to encompass variations in the anatomy which may be found in that region. Thus a device which covers the ostium of the brachiocephalic artery is to be viewed as covering an individual anatomy in which the right common carotid artery branches from the brachiocephalic artery after it leaves the aorta as well as an individual anatomy in which the right common carotid artery connects directly to the aorta. In either anatomy, the debris deflector should be viewed as protecting at least the right common carotid artery and the left common carotid artery.

As intravascular approaches to heart surgery have become more common, it has become more desirable to provide devices which filter or divert emboli or other debris from reaching the carotid arteries, and thereby to reduce the incidence of ischemic stroke, while at the same time maintaining access to the heart tissue for other medical devices.

Figure 1:
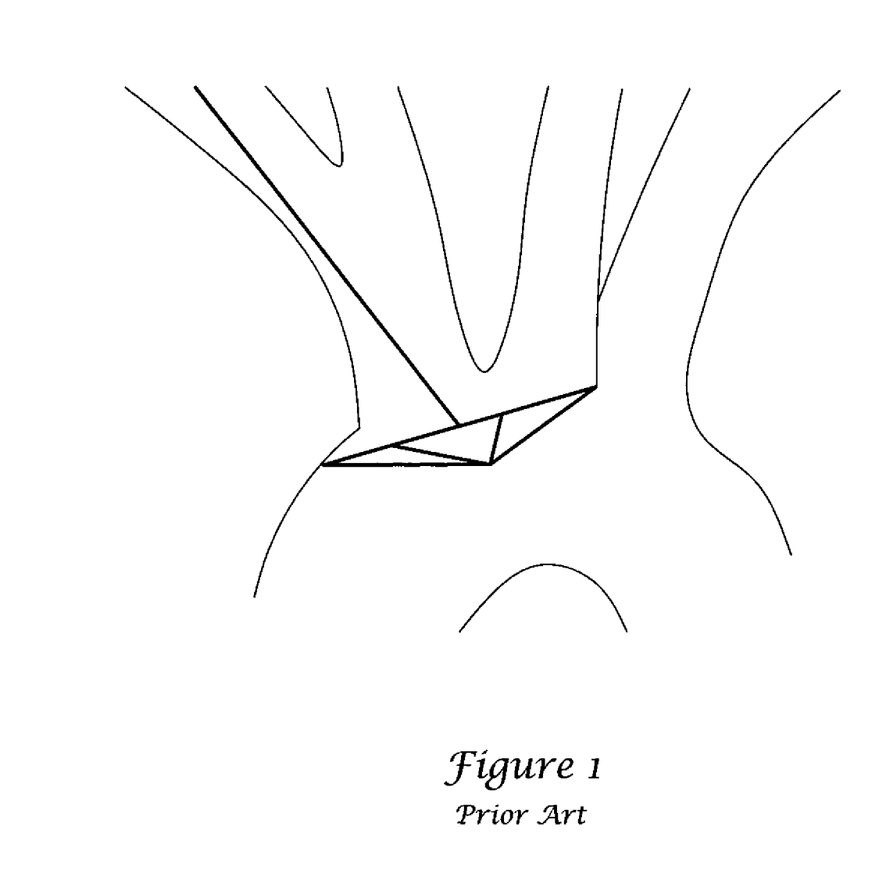
FIG. 1 illustrates a prior art umbrella filter deployed through the right subclavian artery.

FIG. 1 shows an exemplary device of the prior art in which an umbrella filter has been introduced into the aorta through the right subclavian artery and the brachiocephalic artery. This approach directs the filter or deflector through a region of the vasculature which is prone to the accumulation of plaques that may become dislodged during insertion and manipulation of the filter and its associated delivery system. Since the device is deployed beyond the brachiocephalic artery it is not positioned to filter debris thus released into the brachiocephalic artery and the debris may potentially enter the right common carotid artery and reach the brain. Other exemplary devices may employ a flat "snowshoe" deflector which bridges the lumen of the aorta, but generally permits any debris released into the brachiocephalic artery to be distributed into the carotid arteries. In some embodiments, the filter or deflector intrudes significantly into the aorta where it may restrict access to the heart by that common avenue.

Figure 2:
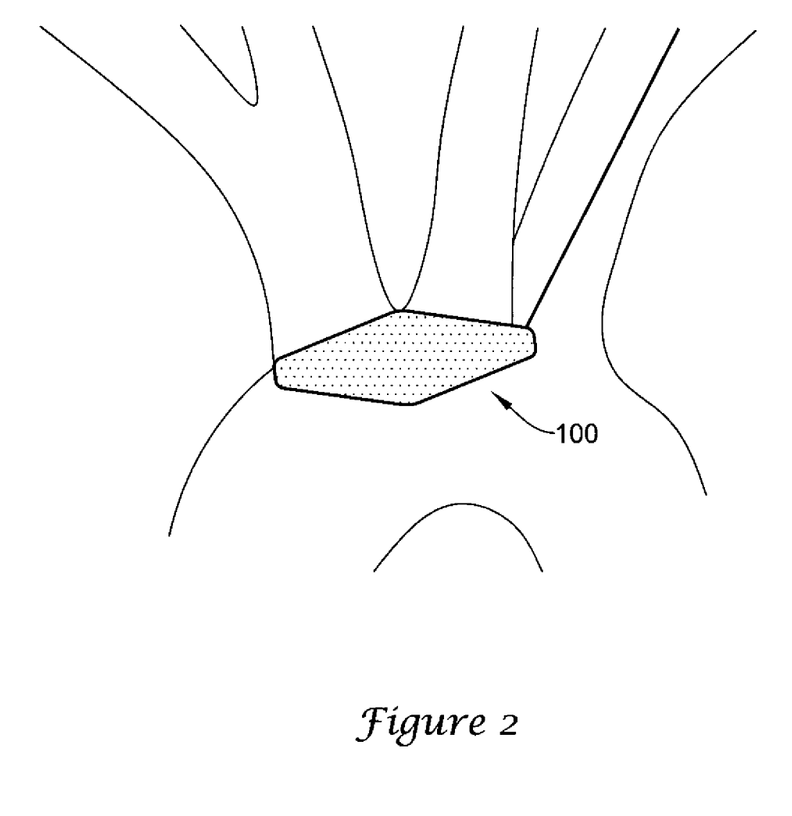
FIG. 2 illustrates an embodiment of the disclosure deployed through the left subclavian artery.

FIG. 2 illustrates somewhat schematically an embodiment of the disclosure in which a debris deflector has been inserted into the aorta through the left subclavian artery and deployed upstream therefrom to cover the ostium of the brachiocephalic artery and thereby access to the right common carotid artery, the ostium of the left common carotid artery, and at least a portion of the ostium of the left subclavian artery. It should be noted that the debris deflector does not significantly enter either the brachiocephalic artery or the left common carotid artery, thus greatly reducing the incidence of release of debris from the walls thereof. The debris deflectors of the disclosure avoid any contact between the deflector and/or the delivery apparatus and the inner surfaces of the carotid arteries and so avoid dislodging plaques which may be present on those surfaces. Although for the purpose of initial schematic illustration the debris deflector has been depicted in a somewhat flattened configuration, it will be appreciated that the deflector may be viewed as a somewhat flexible filtration membrane which may be flattened against the aortic arch by blood flow or by support structures thereby maintaining interventional or diagnostic access through the aorta. Insertion through the left subclavian artery into the aorta will be presumed in the descriptions which follow; however it will be appreciated that the disclosed debris diverter may be delivered by different routes and may be employed in other portions of the anatomy with appropriate modification, if desired.

Figure 3:
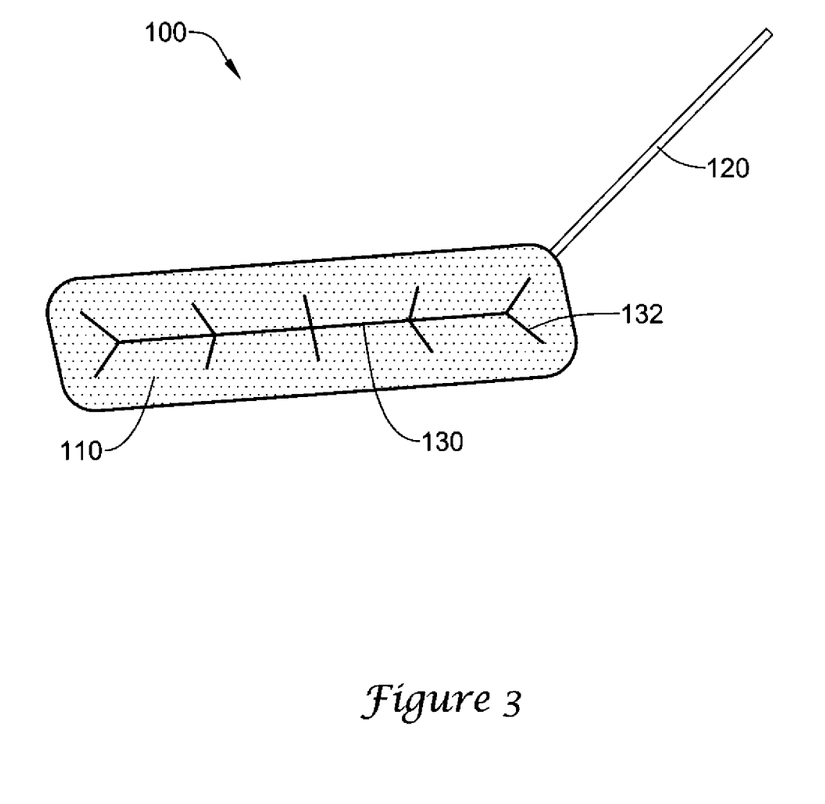
FIG. 3 illustrates an embodiment of the disclosure.

FIG. 3 illustrates a debris diverter 100 of the disclosure in a flattened and unconstrained state. The debris diverter 100 comprises a single panel blood permeable membrane having a plurality of openings therethrough sized to pass blood cells while rejecting larger debris such as emboli. In the embodiment of FIG. 3 the single panel blood permeable membrane is supported by a support structure comprising a central longitudinal spine 130 and a plurality of generally transverse branches 132 therefrom which bias the support structure 130, 132 to conform to the wall of the aorta when the longitudinal spine 130 is urged against the aortic wall. The transverse cross-sections of the longitudinal spine 130 and the generally transverse branches 132, as well as any perimeter support component of the support structure, may be of any convenient form such as round, oval, rectangular, and the like. The central spine 130 may be a continuation of elongated support member 120 or may be a separate element attached to the distal end of the elongated support member 120. The central spine 130 may be attached to the elongated support member 120 by a deformable joint which straightens for deployment and retrieval and deflects to position the blood permeable membrane generally along the wall of the aorta upon release within the aorta. Other configurations of the joint will be discussed herein with regard to FIGS. 7-9.

In the embodiment of FIG. 3, the illustrated support structure 130, 132 does not include an optional perimeter component. Although a single non-limiting pattern of transverse branches has been illustrated, it will be appreciated that other patterns may also be employed. For example, the generally transverse branches 132 may be arranged in a pattern resembling the veins of a leaf, including additional sub-branches (not shown); in a fishbone-like pattern (not shown) in which the generally transverse branches are parallel; lattice-like arrangements in which a plurality of transverse branches are combined with a plurality of longitudinal members; and the like. The pattern of support structural members may be symmetric or asymmetric about the central spine 130. Although the embodiment depicted includes a single panel of blood permeable membrane, the point of attachment between the elongate support member 120 and the central spine 130 may be such that the panel is effectively divided into a distal portion and a proximal portion. Such an arrangement may be desirable if more complete coverage of the ostium of the left subclavian artery is desired. It is generally desirable that the blood permeable membrane 110 lie along the wall of the aorta along its perimeter, although this is not an absolute requirement and the diversion of the major blood flow may suffice to exclude the majority of the blood flow volume, and thus any debris, from the region proximate the wall of the aorta.

In this and other embodiments, the blood permeable membrane may be attached to the support structure(s) along the entire length of the support structure or may be attached only periodically thereby allowing the blood permeable membrane to conform somewhat more closely to the aortic wall, for example by billowing toward the aortic wall under the influence of blood flow. The support structure 130, 132 comprises a biocompatible material such as a polymer or metal. In some embodiments, the biocompatible material may be a shape memory material adapted to bias the porous deflection structure toward a deployed configuration in which the blood permeable membrane 110 lies generally against the wall of the aorta when deployed therein.

In some embodiments, the blood permeable membrane 110 may be formed from a woven or nonwoven fabric, from a perforated membrane, or from other materials known in the art for that purpose. In certain embodiments the blood permeable membrane 110 may include regions of differing elasticity. For example, the central portion of the blood permeable membrane 110 may be somewhat more elastic than the region(s) near the perimeter thereby allowing the permeable membrane 110 to deflect to a degree into the various ostia to provide a better seal and/or to limit the longitudinal migration of the debris deflector under the influence of blood flow. The blood permeable membrane 110 may comprise a biocompatible material such as a polymer or metal.

In certain embodiments, the blood permeable membrane 110 and the associated support structure 130, 132 may be formed from the same material while in other embodiments, the blood permeable membrane 110 and the associated support structure 130, 132 may be formed from different materials. Similarly, it is not necessarily the case that all portions of the support structure be formed of the same material. For example, the central spine may be formed from one material while some or all of the laterally extending branches may be formed from a different material. In yet other embodiments, the blood permeable membrane and the associated support structure may be integrally formed in a single step as by, for example, injection molding. In many embodiments, both the blood permeable membrane and the support structure may exhibit a degree of elastic response which allows the blood permeable membrane and support structure to be furled or otherwise compacted for delivery and/or retrieval. Similar material considerations apply to components of other embodiments disclosed herein.

Figure 4:
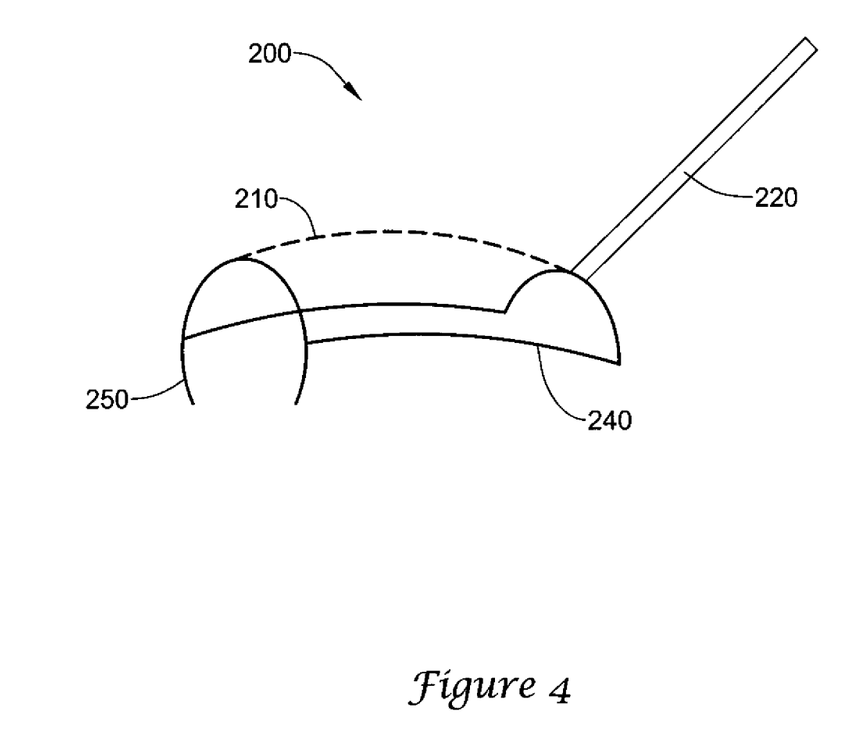
FIG. 4 illustrates another embodiment of the disclosure.
Figure 5:
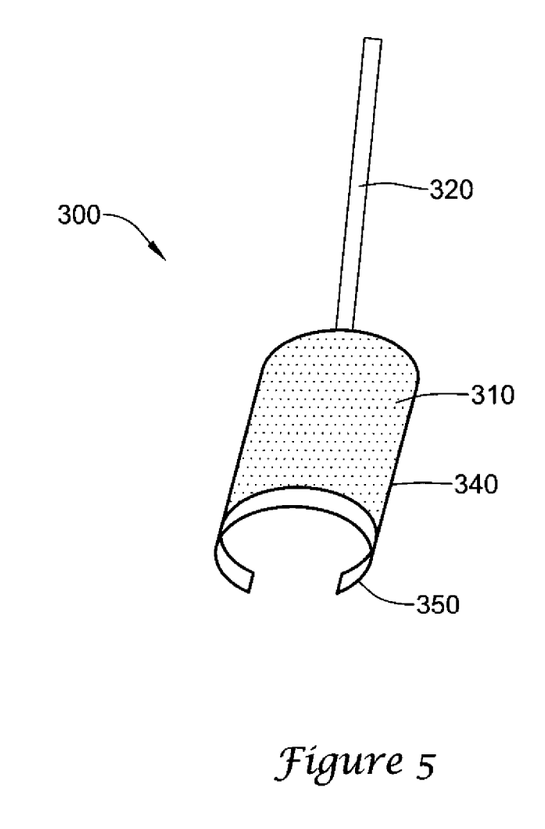
FIG. 5 illustrates a variation of the embodiment of FIG. 4.

In the embodiment illustrated in FIG. 4, the support structure for the blood permeable member is provided by a perimeter support component 240 attached to the distal end of elongate support member 220. The perimeter support component 240 includes distal and proximal arches which are depicted as generally parallel and perpendicular to the longitudinal members of the perimeter support component 240; however it will be understood that it would be within the skill of one in the art to incline the arches to lie generally transverse to the aorta at those points. The perimeter support component 240 illustrated in FIG. 4 includes optional distal positioning members 250 extending the distal arch which may serve to urge the distal end of the blood permeable membrane more firmly against the aorta wall than would be the case if the elongate support member 220 were to be used alone for positioning the device within the aorta. The optional distal positioning members 250 may serve to further ensure that the lumen of the aorta remains free of obstruction which might limit intravascular access through the aorta. The optional distal positioning members 250 may also help to stabilize the position of the porous deflection structure during pulsate blood flow which tends to cause the aorta to expand and contract. FIG. 5 illustrates a similar porous deflection structure in which the optional distal positioning members 350 are present in the form of a partial collar which may distribute positioning forces applied to the aorta to reduce the chance of injury.

The presence and extent of a blood permeable membrane (omitted for clarity) is indicated by the reference numeral 210 in FIG. 4 which shows that the blood permeable membrane is biconvex outward toward the wall of the aorta to allow it to conform more closely to the surface of the aortic arch.

Figure 6:
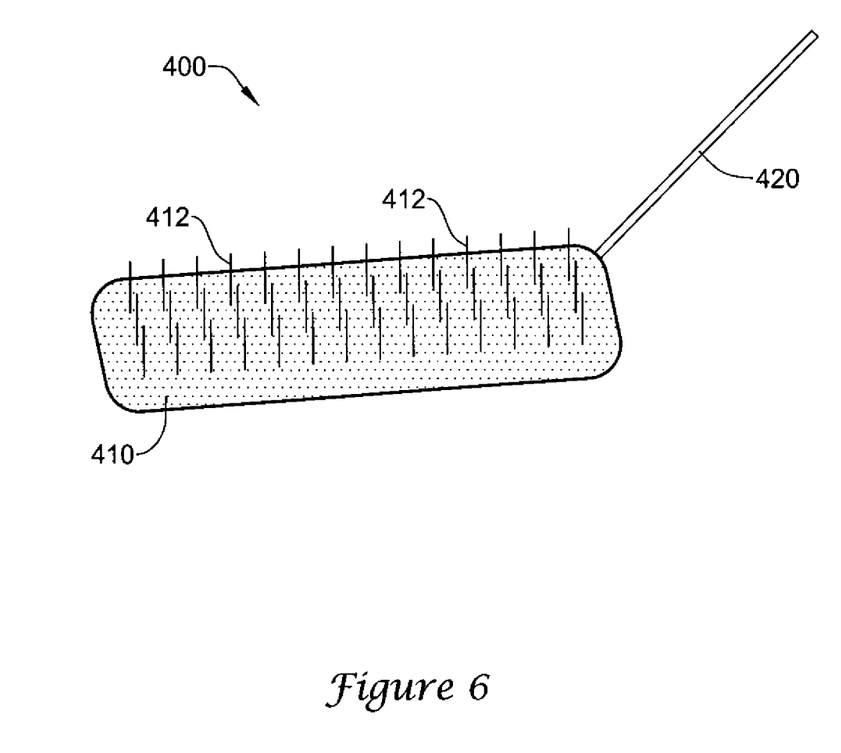
FIG. 6 illustrates a variation of a porous deflection structure of the disclosure.

FIG. 6 is representative of contemplated variations in the surface of the porous deflection surface presented by the embodiments of FIGS. 3-5. The blood permeable membrane 410 includes a plurality of bristles 412 which may provide a trapping texture for at least some of the debris which may be deflected past the porous deflection surface. To the extent that debris is trapped by the bristles 412, it may be removed with the debris deflector and prevented from reaching other portions of the body. In some embodiments, the bristles 412 may project toward the adjacent wall of the aorta to improve the seal between the aorta wall and the porous deflection body. In other embodiments, the bristles 412 may project away from the aorta wall and into the deflected flow. In yet other embodiments, bristles 412 may be provided on both surfaces of the blood permeable membrane 410.

Figure 7:
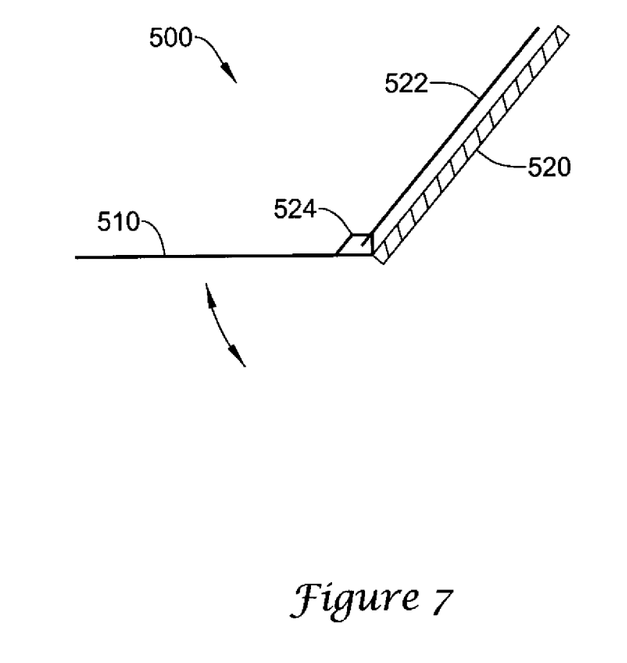
FIGS. 7-9 illustrate exemplary actuation systems which may be employed with embodiments of the disclosure.
Figure 8:
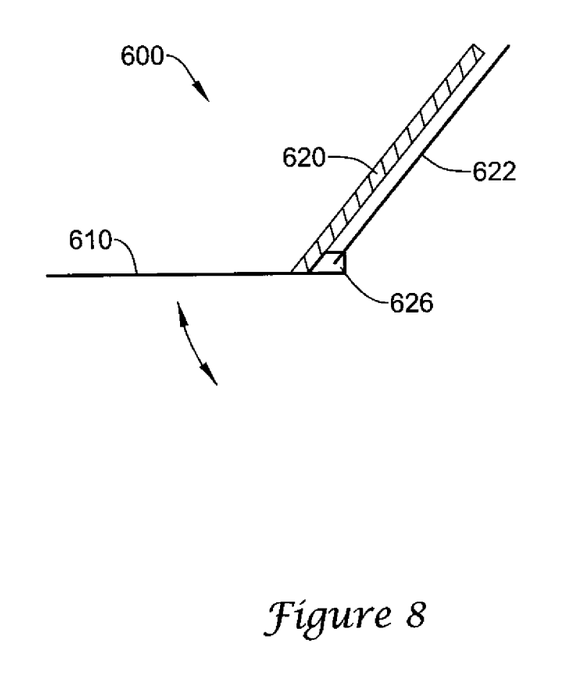
Figure 9:
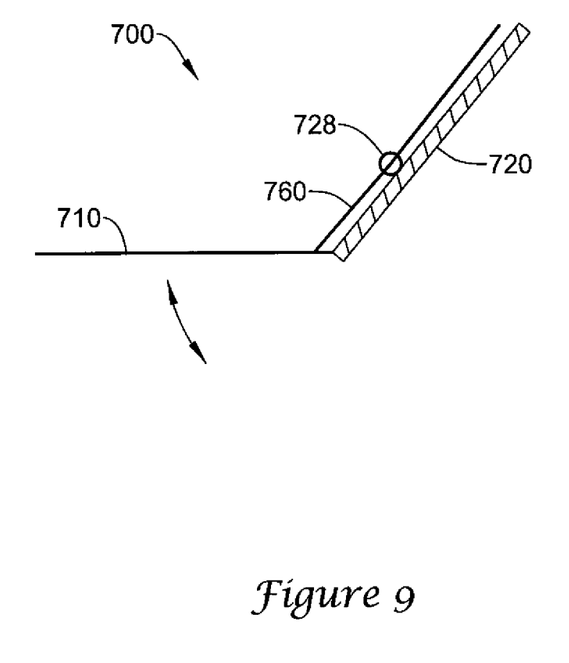

FIGS. 7-9 represent alternate methods of employing an actuator 522, 622, 760 in conjunction with a porous deflection surface 510, 610, 710 and an elongate support member 520, 620, 720. In FIG. 7, the actuator, pull rod or wire 522 is attached to the porous deflection surface 510, here indicated as a flat surface for clarity rather than as a curved or deformable surface as depicted in FIGS. 3-6, at attachment point 524 located distal of the join between elongated support member 520 and the porous deflection surface 510. The join may be flexible and/or resilient as discussed herein, or may be a hinge located proximate the proximal end of porous deflection surface 510. Pulling on pull rod or wire 522 deflects the porous deflection surface 510 such that it is urged toward the aortic wall in the region containing the ostia of the brachiocephalic artery and/or the right common carotid artery and the left common carotid artery. In some embodiments, pushing on the pull rod or wire 522 may tend to straighten the connection between the porous deflection surface 510 and the elongate support member 520 to facilitate retrieval following a procedure.

In FIG. 8, the actuator, push rod or wire 622 is attached to the porous deflection surface 610, here indicated as a flat surface for clarity rather than as a curved or deformable surface as depicted in FIGS. 3-6, at attachment point 626 located proximal of the join between elongated support member 620 and the porous deflection surface 610. The join may be flexible and/or resilient as discussed herein, or may be a hinge located proximate the proximal end of porous deflection surface 610. Pushing on push rod or wire 622 deflects the porous deflection surface 610 such that it is urged toward the aortic wall in the region containing the ostia of the brachiocephalic artery and the left common carotid artery. In some such embodiments, pulling on the push rod or wire 622 may tend to straighten the connection between the porous deflection surface 610 and the elongate support member 620 to facilitate retrieval following a procedure.

In FIG. 9, the actuator, tether 760 is attached to the porous deflection surface 710, here indicated as a flat surface for clarity rather than as a curved or deformable surface as depicted in FIGS. 3-6, at attachment point located distal of the join between elongated support member 720 and the porous deflection surface 710. Tether 760 passes through aperture 728 associated with elongate support member 720. The join may be flexible and/or resilient as discussed herein, or may be a hinge located proximate the proximal end of porous deflection surface 710. Pulling on tether 760 deflects the porous deflection surface 710 such that it is urged toward the aortic wall in the region containing the ostia of the brachiocephalic artery and/or the right common carotid artery and the left common carotid artery. In some such embodiments, relaxing tension on tether 760 may tend to allow the join to straighten between the porous deflection surface 710 and the elongate support member 720 to facilitate retrieval following a procedure.

It will be appreciated that pull rod or wire 522, push rod or wire 622, or tether 760 may be disposed alongside the respective elongate support members 520, 620, 720 or may enter and be disposed within a lumen (not shown) of respective elongate support members 520, 620, 720 to become available for manipulation external to the body.

Figure 10:
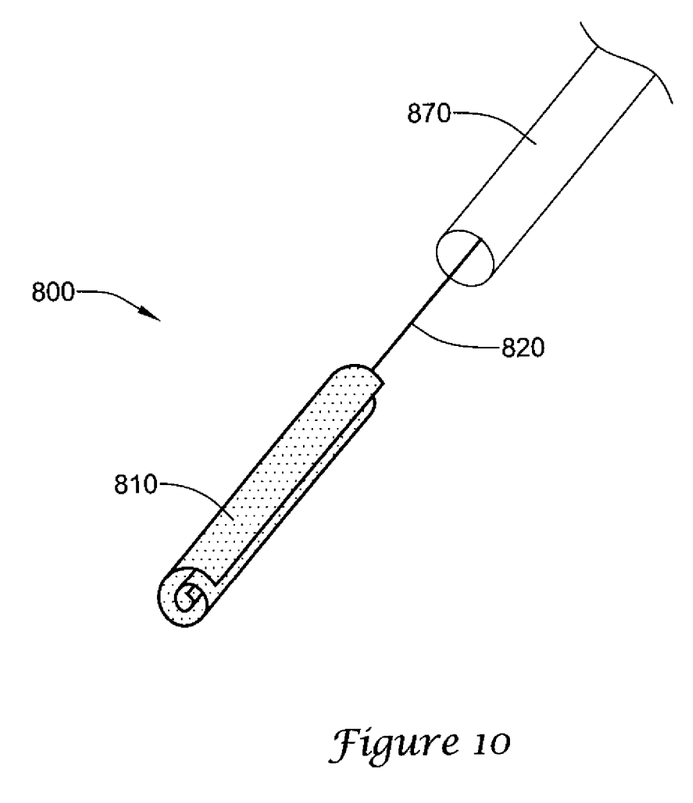
FIG. 10 illustrates an exemplary deployment/retrieval system of the disclosure.

In FIG. 10, a debris deflector 800 of the disclosure may be combined with a delivery device 870 and/or a retrieval device 870 to form a system for preventing debris within the aorta from entering the right carotid artery and the left carotid artery. The delivery/retrieval device 870 may comprise a catheter having a distal lumen adapted to at least partially contain the debris deflector 800 in a delivery/retrieval configuration or may comprise other delivery/retrieval devices known in the art. In some embodiments, the distal mouth of the delivery/retrieval device 870 may include one or more features (not shown) adapted to engage an edge or edges of the porous deflection structure 810 of the debris deflector 800 to assist in unfurling or furling the porous deflection structure 810 during delivery/retrieval by providing an initial twist in an appropriate direction.

The debris deflectors of the disclosure may be employed by advancing the debris deflector, optionally at least partially disposed within a lumen of a delivery device, percutaneously and intravascularly through the left subclavian artery and into the aorta. Upon reaching the aorta, the porous deflection structure of the debris deflector may be advanced upstream of the left subclavian artery such that the distal end of the debris deflector extends distal of the ostium of the brachiocephalic artery and then may be urged against the wall of the aorta proximate the brachiocephalic artery, the right common carotid artery, the left common carotid artery, and at least a portion of the left subclavian artery. If desired, the porous deflection structure of the debris deflector may fully cover the ostium of the left subclavian artery as well as the ostium of the brachiocephalic artery. Positioning of the porous deflection structure of the debris deflector may be assisted by the presence of an actuator and/or one or more optional distal positioning members. At this point, a diagnostic and/or therapeutic procedure may be performed upstream of the aorta with a greatly reduced risk that any debris which may reach the aorta will enter either the right common carotid artery or the left common carotid artery. Following the completion of the diagnostic and/or therapeutic procedure, the porous deflection structure of the debris deflector may be withdrawn from the aorta, optionally first at least partially entering lumen of a retrieval device, and then removed from the body through the left subclavian artery.

Although the illustrative examples described above relate to the prevention of debris within the aorta entering the right common carotid artery and the left common carotid artery by inserting a debris deflector into the aorta through the left subclavian artery, other uses within the body are also contemplated. In such an embodiment, size and shape of the porous deflection structure of the debris deflector may require modification to reflect the geometry of the use site within the body and the vessel(s) to be protected.

Various modifications and alterations of this disclosure will become apparent to those skilled in the art without departing from the scope and principles of the disclosure, and it should be understood that this disclosure is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A debris deflector comprising:
an elongate support member and
a porous deflection structure adapted to lie substantially along a longitudinal segment of an aortic arch while extending transversely about less than an entire circumference of the aorta,
wherein the porous deflection structure comprises a single panel blood permeable membrane and a support structure,
wherein the single panel blood permeable membrane of the porous deflection structure further includes a plurality of projections which provide a trapping texture extending substantially perpendicular to the support surface of the single panel blood permeable membrane,
wherein the support structure comprises a central spine and a plurality of laterally extending branches,
wherein the plurality of laterally extending branches of the support structure are biased to assume a configuration which is convex toward the wall of the aorta proximate the brachiocephalic artery, the right common carotid artery, and the left common carotid artery and further wherein the central spine of the support structure is convex along the wall of the aorta proximate the brachiocephalic artery and the left common carotid artery,
wherein the elongate support member and porous deflection structure are adapted to be delivered to an aorta via the left subclavian artery and to deploy generally upstream therefrom to cover the ostium of the brachiocephalic artery, the ostium of the right common carotid artery, the ostium of the left common carotid artery, and at least a portion of the ostium of the left subclavian artery.

2. The debris deflector of claim 1, wherein the porous deflection structure is free of a perimeter support component.

3. The debris deflector of claim 1, wherein the single panel blood permeable membrane of the porous deflection structure is a woven fabric.

4. The debris deflector of claim 1, wherein the single panel blood permeable membrane of the porous deflection structure is a nonwoven fabric.

5. The debris deflector of claim 1, wherein the single panel blood permeable membrane of the porous deflection structure is a perforated membrane.

6. The debris deflector of claim 1, wherein the single panel blood permeable membrane of the porous deflection structure is integrally formed with the central spine and the plurality of laterally extending branches.

7. The debris deflector of claim 1, wherein the single panel blood permeable membrane of the porous deflection structure comprises a biocompatible polymer.

8. The debris deflector of claim 1, wherein the single panel blood permeable membrane of the porous deflection structure comprises a biocompatible metal.

9. The debris deflector of claim 1, wherein at least one of the central spine and the plurality of laterally extending branches of the porous deflection structure comprises a biocompatible polymer.

10. The debris deflector of claim 1, wherein at least one of the central spine and the plurality of laterally extending branches of the porous deflection structure comprises a biocompatible metal.

11. The debris deflector of claim 9, wherein at least one of the central spine and the plurality of laterally extending branches of the porous deflection structure comprises a shape memory material.

12. The debris deflector of claim 1, wherein the support structure of the porous deflection structure includes a perimeter support component along at least a portion of a perimeter of the single panel blood permeable membrane.

* * * * *